United States Patent
Seeber et al.

(10) Patent No.: US 10,813,707 B2
(45) Date of Patent: Oct. 27, 2020

(54) METHOD FOR THE APPROVAL CONTROL OF A SURGICAL INSTRUMENT TO BE USED IN A SURGICAL ROBOT SYSTEM AND SURGICAL ROBOT SYSTEM

(71) Applicant: avateramedical GmbH, Jena (DE)

(72) Inventors: Marcel Seeber, Jena (DE); Roberto Witt, Jena (DE)

(73) Assignee: avateramedical GmbH, Berlin (DE)

( * ) Notice: Subject to any disclaimer, the term of this patent is extended or adjusted under 35 U.S.C. 154(b) by 176 days.

(21) Appl. No.: 16/100,331

(22) Filed: Aug. 10, 2018

(65) Prior Publication Data

US 2019/0046282 A1 Feb. 14, 2019

(30) Foreign Application Priority Data

Aug. 11, 2017 (DE) .................. 10 2017 118 347

(51) Int. Cl.
*A61B 34/35* (2016.01)
*A61B 34/30* (2016.01)
(Continued)

(52) U.S. Cl.
CPC .............. *A61B 34/35* (2016.02); *A61B 34/25* (2016.02); *A61B 34/30* (2016.02); *A61B 90/98* (2016.02);
(Continued)

(58) Field of Classification Search
CPC ......... A61B 34/35; A61B 34/30; A61B 90/98; A61B 34/25
See application file for complete search history.

(56) References Cited

U.S. PATENT DOCUMENTS

2002/0032452 A1 * 3/2002 Tierney .................. G06Q 30/02
606/130
2003/0135203 A1 * 7/2003 Wang ..................... G05B 15/02
606/1
(Continued)

FOREIGN PATENT DOCUMENTS

EP 1146830 B1 4/2010
EP 2298219 B1 4/2016
(Continued)

OTHER PUBLICATIONS

European Search Report in corresponding application EP18186945.

*Primary Examiner* — Richard G Louis
(74) *Attorney, Agent, or Firm* — McGarry Bair PC

(57) ABSTRACT

A surgical robot system includes a manipulator for a surgical instrument intended for use in one single operation, a control unit for controlling the manipulator, and a read and write device for reading and storing data of a data memory. The read and write device is configured to read out first data with first information on the surgical instrument from the data memory and to transmit them to the control unit when the surgical instrument is coupled with the robot system. The control unit checks whether at least the one compatibility criterion meets at least one compatibility condition stored in the control unit in a preset manner based on the second information. The control unit approves the surgical instrument for use by the surgical robot system only when the compatibility criterion meets the at least one compatibility condition stored in a preset manner.

16 Claims, 6 Drawing Sheets

(51) Int. Cl.
*A61B 90/98* (2016.01)
*A61B 34/00* (2016.01)
A61B 90/00 (2016.01)
G16H 40/60 (2018.01)

(52) U.S. Cl.
CPC ......... *A61B 34/70* (2016.02); *A61B 2034/302* (2016.02); *A61B 2090/0814* (2016.02); *G16H 40/60* (2018.01)

(56) References Cited

U.S. PATENT DOCUMENTS

| | | | |
|---|---|---|---|
| 2008/0020714 A1* | 1/2008 | Mezhinsky | A61F 9/008 455/73 |
| 2008/0221443 A1 | 9/2008 | Ritchie et al. | |
| 2008/0281301 A1 | 11/2008 | DeBoer et al. | |

FOREIGN PATENT DOCUMENTS

| | | |
|---|---|---|
| EP | 2363091 B1 | 4/2016 |
| WO | 94/14129 | 6/1994 |

\* cited by examiner

METHOD FOR THE APPROVAL CONTROL OF A SURGICAL INSTRUMENT TO BE USED IN A SURGICAL ROBOT SYSTEM AND SURGICAL ROBOT SYSTEM

CROSS REFERENCE TO RELATED APPLICATION

This application claims the benefit of German Application DE 10 2017 118 347.7, filed on Aug. 11, 2017, which is incorporated herein in its entirety.

BACKGROUND

The invention relates to a method for the approval control of a surgical instrument to be used in a surgical robot system, and a surgical robot system with at least one manipulator for moving and/or actuating a surgical instrument which is intended for use in one single operation.

Such methods and surgical robot systems, respectively, are used in the field of surgery so that a reliability of the robot systems can be guaranteed and a misuse of instruments in the surgical field can be avoided.

From the prior art it is known that when coupling a surgical instrument to a robot system necessary data are provided to the robot system for characterizing the instrument to be coupled. Thus, from EP 1 146 830 B1, a surgical robot system having a processor and a tool holder and at least one surgical robot tool is known. The robot tool comprises a shaft with a proximal end and a distal end, an interface at the proximal end of the shaft, wherein it is possible to mount the interface on the tool holder. Further, the tool comprises an end effector which is coupled to the distal end of the shaft, the end effector being movable relative to the shaft in at least one degree of freedom. A drive system is provided that is coupled to the interface to drive at least one element of the end effector that is movable in at least one further degree of freedom. A circuitry is coupled to the interface to provide the processor with a signal that indicates a tool type of the tool and a range of movement of the end effector in the at least one degree of freedom.

The processor is configured such that it determines the tool type and the range of movement of the end effector of a tool held by the tool holder on the basis of the signal that is provided by the circuitry coupled to the interface of the surgical robot tool. Further, the signal indicates the tool life and/or the cumulated tool use by a measurement of a calendrical date, a time, a number of surgical procedures, a number of cases in which the tool had been coupled to the system, or a number of end effector actuations.

From EP 2 298 219 B1, a surgical robot tool for use in a surgical robot system is known, comprising a processor instructing the movement of a tool holder. The tool comprises a probe having a proximal end and a distal end, a surgical end effector disposed adjacent to the distal end of the probe, and an interface disposed adjacent to the proximal end of the probe. The interface comprises a circuitry mounted on the probe and emitting a signal to the processor via the interface. The tool is characterized in that the signal defines tool calibration offsets between a nominal relative position of the section of the drive system and the surgical end effector and a measured relative position of the section of the drive system and the surgical end effector.

The signal comprises unique tool identification data or indicates at least a tool life and a cumulated tool use by a measurement of a calendrical date, a time, a number of surgeries, a number of coupling operations, in which the tool had been coupled to the system, or a number of end effector actuations.

EP 2 363 091 B1 discloses a surgical robot system with a surgical tool, a robot manipulator with a tool holder to which the surgical tool may be releasably coupled. The robot manipulator is designed to manipulate the surgical tool such that the surgical tool moves, and with a processor for controlling the robot manipulator so that it controls the movement of the surgical tool. The surgical tool has a probe with a proximal and a distal end, a surgical end effector disposed adjacent to the distal end of the probe, an interface disposed adjacent to the proximal end of the probe, wherein the interface can be releasably coupled to the tool holder, as well as a circuitry mounted on the probe.

The circuitry defines a signal for transmission to the processor to indicate the compatibility of the tool with the system, the signal comprising unique identification data and an encoded verification data sequence which is calculated from the unique identification data according to an algorithm. Here, the processor is configured for receiving the signal from the tool when it is coupled to the tool holder, manipulating the unique identification data with the algorithm to generate confirmation data, comparing the confirmation data with the encoded verification data sequence to verify the compatibility of the tool with the surgical robot system and allowing that the surgical robot system manipulates the tool when the confirmation data correspond to the encoded verification data sequence.

In addition, in particular with respect to instruments which are intended for a use in one single operation only, so-called one-time instruments, there is a need to guarantee that sterilization requirements on surgical instruments are kept.

SUMMARY OF THE INVENTION

Thus, the invention provides a method and a surgical robot system by which an unauthorized use of a surgical instrument including an unintended multiple use of such an instrument can be ruled out. In particular, a multiple use of a one-time instrument which has already been used in a medical surgery shall be ruled out. Likewise, a use of a surgical instrument shall be ruled out when at least one predeterminable parameter of the instrument does not show a required device value or does not meet the admissible device value.

According to a first aspect, the invention provides a method for the approval control of a surgical instrument that is to be used in a surgical robot system and has a data memory in which first data with first information on the surgical instrument and second data with information on at least one compatibility criterion of the surgical robot system with respect to the surgical instrument are stored. In this method, the surgical instrument is coupled to the surgical robot system, the first data are read from the data memory, and by means of the first information contained in the first data it is checked whether the surgical instrument is suitable for use in the surgical robot system. If, upon checking, a suitability of the surgical instrument for use in the surgical robot system is determined, the second data are read from the data memory and with the aid of the second information contained in the second data it is checked whether at least the one compatibility criterion meets at least one compatibility condition stored in a preset manner in the surgical robot system. Further, in the method the surgical instrument is only approved for use by the surgical robot system when the compatibility criterion meets the at least one compatibility condition stored in a preset manner. In this way, it can be guaranteed both that the instrument is suitable for the robot system at all, i.e. is compatible, and that the instrument may only be used in one single surgery so that the same instrument cannot be used in a surgery of another patient, neither inadvertently nor deliberately.

According to a second aspect, the invention provides a surgical robot system having at least one manipulator for movement and/or actuation of a surgical instrument, which is in particular intended for use in one single surgery, comprising a control unit for controlling the manipulator, a read and write device for reading and storing data of a data memory of the surgical instrument. In connection with a coupling of the surgical instrument with the robot system, the read and write device is configured to read first data with first information on the surgical instrument from the data memory and to transmit them to the control unit.

The surgical robot system is characterized in that the data memory of the surgical instrument contains second data with information on at least one compatibility criterion of the surgical robot system with respect to the surgical instrument, that the read and write device, in connection with the coupling of the surgical instrument to the robot system, is configured to read at least the first data from the data memory and to transmit them to the control unit, and that the control unit is configured to check with the aid of the first information contained in the first data whether the surgical instrument is suitable for use in the surgical robot system. Further, the surgical robot system is characterized in that the read and write device reads the second data from the data memory and transmits them to the control unit when the control unit, upon checking, has determined a suitability of the surgical instrument for use in the surgical robot system. Moreover, the surgical robot system is characterized in that the control unit is configured to check on the basis of the second information contained in the second data whether at least the one compatibility criterion meets at least one compatibility condition stored in the control unit in a preset manner, and that the control unit only approves the surgical instrument for use by the surgical robot system whenever the compatibility criterion meets the at least one compatibility condition stored in a preset manner.

The robot system or a control unit of the robot system can substantially perform the method steps of the method according to claim 1 to ensure both that the instrument is suitable for the robot system at all, i.e. is compatible, and that the instrument can only be used in one single surgery so that the same instrument cannot be used in a surgery of another patient, neither inadvertently nor deliberately.

Thus, the method according to the first aspect and the robot system according to the second aspect have the advantage to ensure in the case of surgeries or operations a compatibility of surgical instrument units or instruments to be used during these surgeries or operations. Further, the invention guarantees that surgical instrument units or instruments can be used both in conformity with the product-relevant specifications and in conformity with the required sterilization criteria.

The robot system according to the second aspect can be developed in the same manner as the method according to claim 1, in particular with the features of the dependent claims. Likewise, the method according to claim 1 can be developed with features of the robot system, in particular with features of the dependent claims.

In one embodiment, the second data contain an information wildcard for adding an operation identification. In a simple design, the information wildcard can be configured as a reserved memory. As a compatibility condition it is checked whether the information wildcard is present in the second data. Further, the compatibility criterion comprises an operation identification that can be predetermined by the robot system, a system operation identification for the unique identification of a single operation in which the surgical instrument is to be used. The system operation identification predetermined by the robot system is stored in the area of the information wildcard of the second data as an instrument operation identification.

In another embodiment, the information wildcard itself establishes a provisional compatibility criterion or includes a provisional compatibility criterion. As a compatibility condition, the presence of the provisional compatibility criterion can be checked.

Further, as a compatibility condition the correspondence of the system operation identification predetermined by the surgical robot system with the instrument operation identification contained in the second data as a compatibility criterion can be checked.

Further, the first data may contain a serial number identifying the surgical instrument at least with respect to its function, a date of manufacture and/or a maximum storage period of the surgical instrument or an expiry date of the surgical instrument, wherein it is checked whether the maximum storage period or the expiry date has been exceeded.

Further, the first or the second data or both data may contain a checksum for their verification. By way of the checksum it can be checked whether the data have been transmitted safely, read out correctly and have not been manipulated.

Further, the first or the second data or both data may be stored and/or transmitted in an encoded manner. An encoding serves for data security. It is also conceivable that the first and/or second data are provided with a write protection, wherein the write protection of the second data is preferably activated after storing the system operation identification and wherein the write protection is preferably no longer deactivatable after activation. The write protection effectively prevents a data manipulation. As a result, it can be guaranteed that in the data memory of the surgical instrument continuously suitable data for its description and identification are provided. In this embodiment of the inventive surgical robot system, the read and write device is designed for decoding and encoding the first and/or the second data.

In a further embodiment, the first data comprise information with a provisional compatibility criterion. These can be realized by binary codes defining a corresponding memory location. What is likewise conceivable is that the information with the provisional compatibility criterion is adapted to the information with the compatibility criterion at least in its data structure or resembles it.

In an advantageous embodiment, the control unit stores the system operation identification, which is stored in a preset manner, as an instrument operation identification in the second data when upon checking no information on a specific operation or surgery is determined in the second data.

Alternatively or additionally, the control unit of an inventive surgical robot system can store the system operation identification, which is stored in a preset manner, as an instrument operation identification in the second data when during a data check in the data memory only an information wildcard is determined.

It can thus be determined that the surgical instrument unit or the surgical instrument is only used for one single, uniquely identified surgical operation.

In the case of a surgical instrument unit intended for use in one single operation or a one-time instrument, a storing of the system operation identification generated by the robot system as an instrument operation identification on the data memory of the instrument unit or the instrument means that the instrument unit or the instrument will be rejected in any further surgical operation identified by a differing system operation identification. The system operation identification can advantageously be composed of alpha-numeric characters. However, a sequence of numbers is likewise conceivable as a system operation identification.

The surgical instrument unit or the surgical instrument is thus marked by the higher robot system or the control unit such that it cannot be coupled to the robot system and used in another operation.

During an approval check of the surgical instrument unit or the surgical instrument, a result of the check may be to mark the surgical instrument unit or the surgical instrument with the system operation identification of a specific operation. That means that the surgical instrument unit or the surgical instrument can be coupled to the robot system, used, again de-coupled and again re-coupled by the control unit or the higher robot system during an operation.

The data memory can be read out by a read and write device of the robot system. The data are evaluated by a control unit of the robot system. A result of the evaluation can be that the surgical instrument unit or the surgical instrument has not yet been used in an operation or that a storage period is shorter than a maximum predetermined storage period so that a use of the surgical instrument unit or the surgical instrument can be approved by the robot system or the control unit.

The first or the second data or both data may contain an information wildcard. The information wildcard may also be generated from other further instrument data contained in the first and/or second data by way of an algorithm.

Further, in addition to the information wildcard the second data may also contain information describing the surgical instrument unit or the surgical instrument such as those information describing the instrument with respect to its function, like scissor, gripper, dissector and the like, a date of manufacture and/or a maximum storage period. As an advantage, a redundancy with respect to the data can be achieved.

In a development, the first data are provided with a write protection, stored in a memory that can only be written once or in a read-only-memory (ROM).

In a preferred embodiment, the control unit is configured to read out and/or to receive the first data and to check the first data.

A further embodiment is characterized in that a checking device for checking the surgical instrument stores the first and/or second data in the data memory of the surgical instrument unit.

In this way, it is possible that during an end check in a corresponding checking device performed at the end of the manufacturing process of the surgical instrument unit or the surgical instrument a serial number unique for the surgical instrument unit and/or the surgical instrument is generated which, together with further information, such as a date of manufacture, a maximum storage period or an expiry date is stored in the first data. When stored, the first data are provided with a checksum, encoded and stored in an allocated data area of the data memory in the surgical instrument unit. After storing the first data, the data area for the first data is usually provided with a write protection.

Likewise, information wildcards for the system operation identification can be stored in the second data of the data memory. This can be a binary sequence of numbers composed of zeros or ones. Preferably, in the information wildcard or also as an information wildcard a provisional compatibility criterion can be stored. Such a provisional compatibility criterion does not yet contain the same information as the system operation identification that can be predetermined by the robot system or is stored therein in a preset manner, but has at least the same data structure.

Within the scope of the end check, in addition to the information wildcards contained in the data memories, further preferably the serial number and further information such as the date of manufacture, the maximum storage period or the expiry date of the surgical instrument unit and/or the surgical instrument can be stored as second data. Then, a redundancy with respect to the data describing the surgical instrument unit or the surgical instrument can be achieved. A data failure or an incorrect readout of for example the first data could be ignored or corrected by the information contained in the second data.

In the method or the robot system, the information wildcard may also be contained in the first data. Then, the provisional compatibility criterion may preferably be used for authentication of the surgical instrument unit or the surgical instrument with the control unit of the robot system. For this, the control unit can calculate the provisional compatibility criterion for example from the further data describing the surgical instrument unit or the surgical instrument by means of an algorithm.

In a further embodiment, the read and write device is configured to read the first data describing the surgical instrument unit or the surgical instrument from the data memory upon a coupling of the surgical instrument unit or the surgical instrument to the robot system. For this, a read out via a short-range transmitting/receiving device, such as an RFID read and write unit can take place so that the data may already be read out when the surgical instrument unit or the surgical instrument have been brought near the robot system within the scope of operation preparations. Likewise, the readout of the data may also take place only after establishing a wired communication connection to the robot system or the control unit.

In a preferred embodiment, the first data contain a date of manufacture and a maximum storage period or an expiry date. The control unit is then configured to check whether the maximum storage period or the expiry date has expired.

Both in the inventive method and in the inventive robot system, a readout or writing of data from the or into the data memory of the surgical instrument unit or the surgical instrument may be accomplished via a radio frequency identification chip (RFID chip or RFID tag). What is likewise conceivable is an optical readout and storage of the data within an optical data transmission. Further, in the case of a wire-bound version, a flash memory may be used. At least the first data could also be provided in a code, such as a quick response (QR) code.

To be able to use both the surgical instrument and the surgical instrument unit in only one single operation, both may have a data memory in which a respective identification uniquely identifying an operation, the system operation identification S-OID, is stored as an instrument operation identification I-OID, preferably in a write-protected manner. As a result, after termination of the operation identified by the system or instrument operation identification either the surgical instrument unit or the surgical instrument can be excluded from further use.

Further features and advantages result from the following description which explains the invention in more detail on the basis of embodiments in connection with the enclosed Figures illustrated at different scales. The illustrated elements are partially illustrated in a simplified manner.

DRAWINGS

DESCRIPTION

Figure 1:
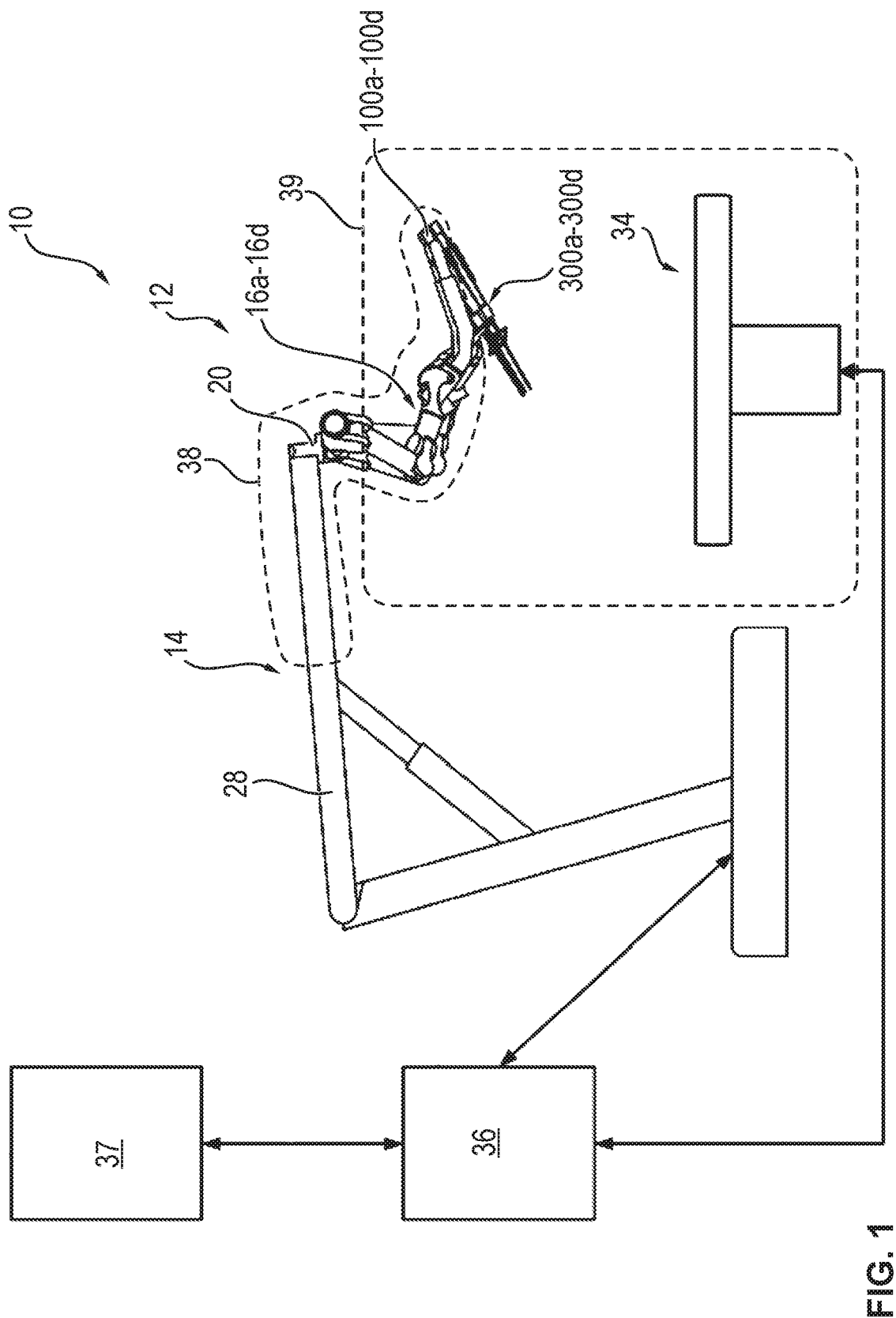
FIG. 1 shows a schematic illustration of a robot system for the robot-assisted surgery with a manipulator having four manipulator arms to each of which one sterile unit of an instrument unit is connectable.

FIG. 1 shows a schematic illustration of the surgical robot system 10 for use in the robot-assisted surgery. The robot system 10 has a manipulator 12 having a stand 14 and preferably four manipulator arms 16*a* to 16*d*. Each manipulator arm 16*a* to 16*d* is connected to a sterile instrument unit 300*a* to 300*d* via a coupling unit 100*a* to 100*d* of the manipulator arm 16*a* to 16*d*.

Figure 2:
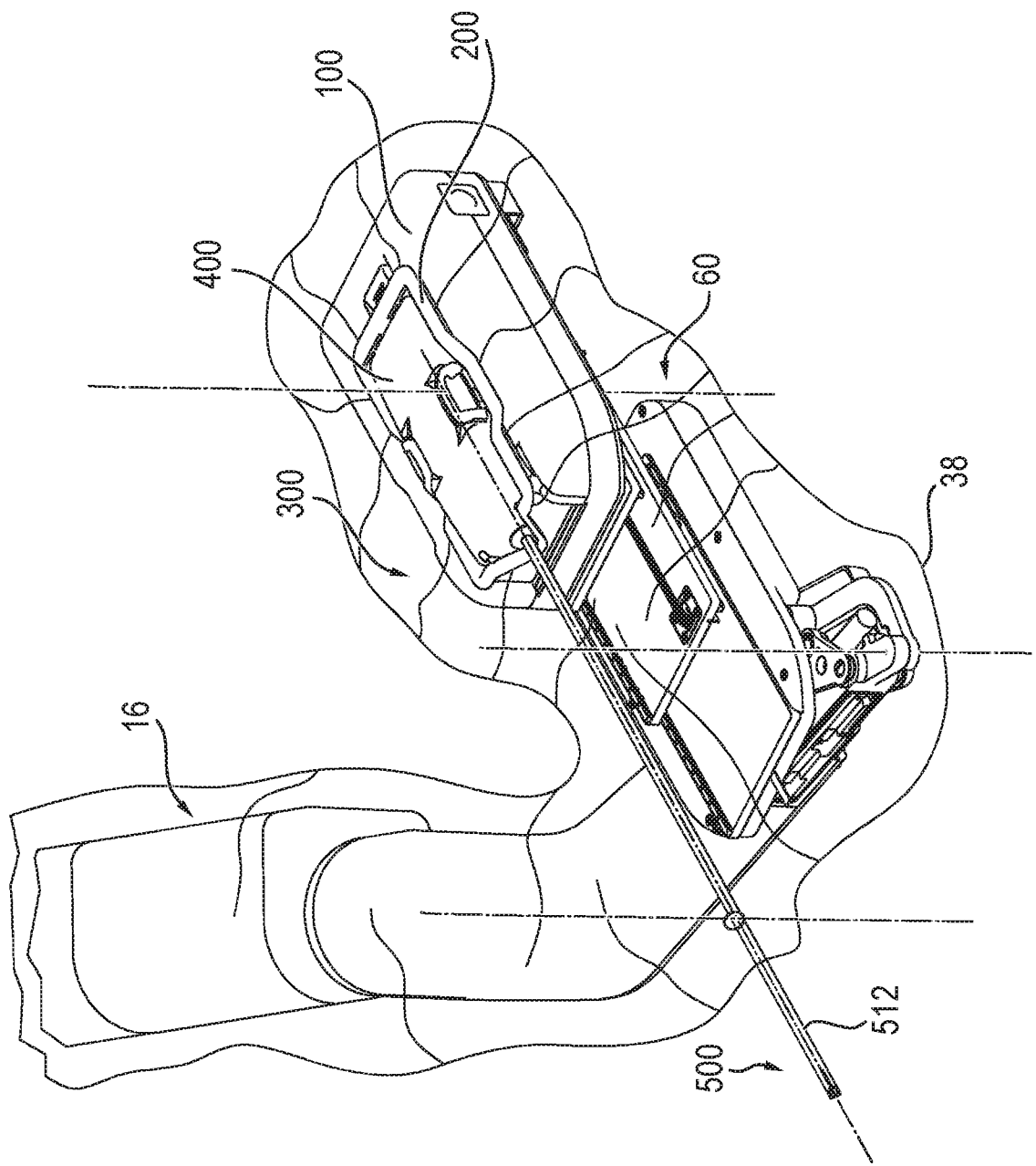
FIG. 2 shows a perspective illustration of a section of a manipulator arm having a coupling unit for coupling the manipulator arm to an instrument unit comprising a sterile unit, with a sterile lock coupled to the coupling unit and a sterile unit of the instrument unit coupled to the sterile lock.

The instrument unit 300*a* to 300*d* is sterile and comprises in addition to a sterile unit 400 that is shown in FIG. 2 and is used for coupling the instrument unit 300*a* to 300*d* with the coupling unit 100*a* to 100*d* of the manipulator arm 16*a* to 16*d* a surgical instrument 500, in particular with an end effector, wherein the end effector can be moved and/or actuated by the coupling unit 100*a* to 100*d* of the manipulator arm 16*a* to 16*d*. As an alternative to the surgical instrument 500, the instrument unit 300*a* to 300*d* may also comprise an optical instrument, in particular an endoscope, and/or a medical device, in particular for applying a medicine, for dispensing a rinsing fluid and/or for aspirating rinsing fluid and/or secretion.

The manipulator 12 is controlled by a control unit 36. Via a data and/or control line, the control unit 36 is connected with an input and output unit 37, which in particular outputs an image of the operation field to a user in real time with the aid of at least one display unit of the input and output unit 37. The user makes user inputs by which the instrument units 300*a* to 300*d* are positioned and actuated during the operation of a patient. Thus, the input and output unit 37 serves as a human-machine interface.

Further, the control unit 36 is connected via a control and/or data line with a non-illustrated control unit of the operating table 34. Via this control and/or data line it is guaranteed that the position of the patient support surface or of segments of the patient support surface of the operating table 34 can only be varied when this is possible without any risk for a patient to be operated due to the positioning of the instruments units 300*a* to 300*d*.

The operating table 34 as well as the instrument units 300*a* to 300*d* are arranged in a sterile operation area 39. The manipulator arms 16*a* to 16*d* and the stand 14 are not sterile. The areas of the manipulator 12 projecting into the sterile operation area 39, i.e. the manipulator arms 16*a* to 16*d*, the stand head 20 and a part of the stand arm 28 are packed in a sterile manner in a sterile flexible sheath 38, such as a sterile foil, indicated by a broken line, so that they may be arranged in the sterile operation area 39 without any risk. The input and output unit 37 is arranged outside the sterile area 39 and thus does not have to be packed in a sterile manner.

In a large number of operations, the instrument units 300*a* to 300*d* have to be changed several times during the operation owing to the course of the operation. Thus, between the manipulator arm 16*a* to 16*d* and the instrument unit 300*a* to 300*d* a sterile interface has to be provided such that the non-sterile parts of the coupling unit of the manipulator arm 16*a* to 16*d* are still covered in a sterile manner even after separation of the instrument unit 300*a* to 300*d*.

In addition, elements of the instrument unit 300*a* to 300*d* contaminated by a contact of the sterile elements with the coupling unit of the manipulator arm 16*a* to 16*d* have to be covered in a sterile manner after separation of the instrument unit 300*a* to 300*d* from the manipulator arm 16*a* to 16*d* so that the instrument unit 300*a* to 300*d* can be placed in the sterile area 39 without contaminating further elements in the sterile area 39. For this, a sterile lock 200 is provided between the coupling unit 100*a* to 100*d* of the manipulator arm 16*a* to 16*d* and the instrument unit 300*a* to 300*d*, which sterile lock has at least one lock flap that is closed when no instrument unit 300*a* to 300*d* is connected to the sterile lock 200 so that then the non-sterile coupling unit 100*a* to 100*d* is shielded from the sterile area 39 by means of the flexible sterile sheath 38 and the sterile lock integrated therein.

In FIG. 2, a section of a manipulator arm 16*a* to 16*d* with a coupling unit 100*a* to 100*d* as well as an instrument unit 300*a* to 300*d* connected with the coupling unit 100*a* to 100*d* via a sterile lock is shown. Since the following explanation is the same for the manipulator arms 16*a* to 16*d* and the instrument units 300*a* to 300*d*, reference is made thereto by using the reference signs 16 and 300. Accordingly, FIG. 2 shows a perspective illustration of a section of a manipulator arm 16 with a coupling unit 100 for coupling the manipulator arm 16 to the instrument unit 300 comprising a sterile unit 400 and an instrument 500. For this, the coupling unit 100 is connected to a sterile lock 200 integrated in a sterile sheath 38. The sterile lock 200 is couplable both to the coupling unit 100 and to a sterile lock 400 and again separable therefrom. In FIG. 2, the sterile lock 200 is illustrated coupled to both the coupling unit 100 and the sterile unit 400. The coupling unit 100 is arranged at the distal end of a telescopic arrangement 60.

Figure 3:
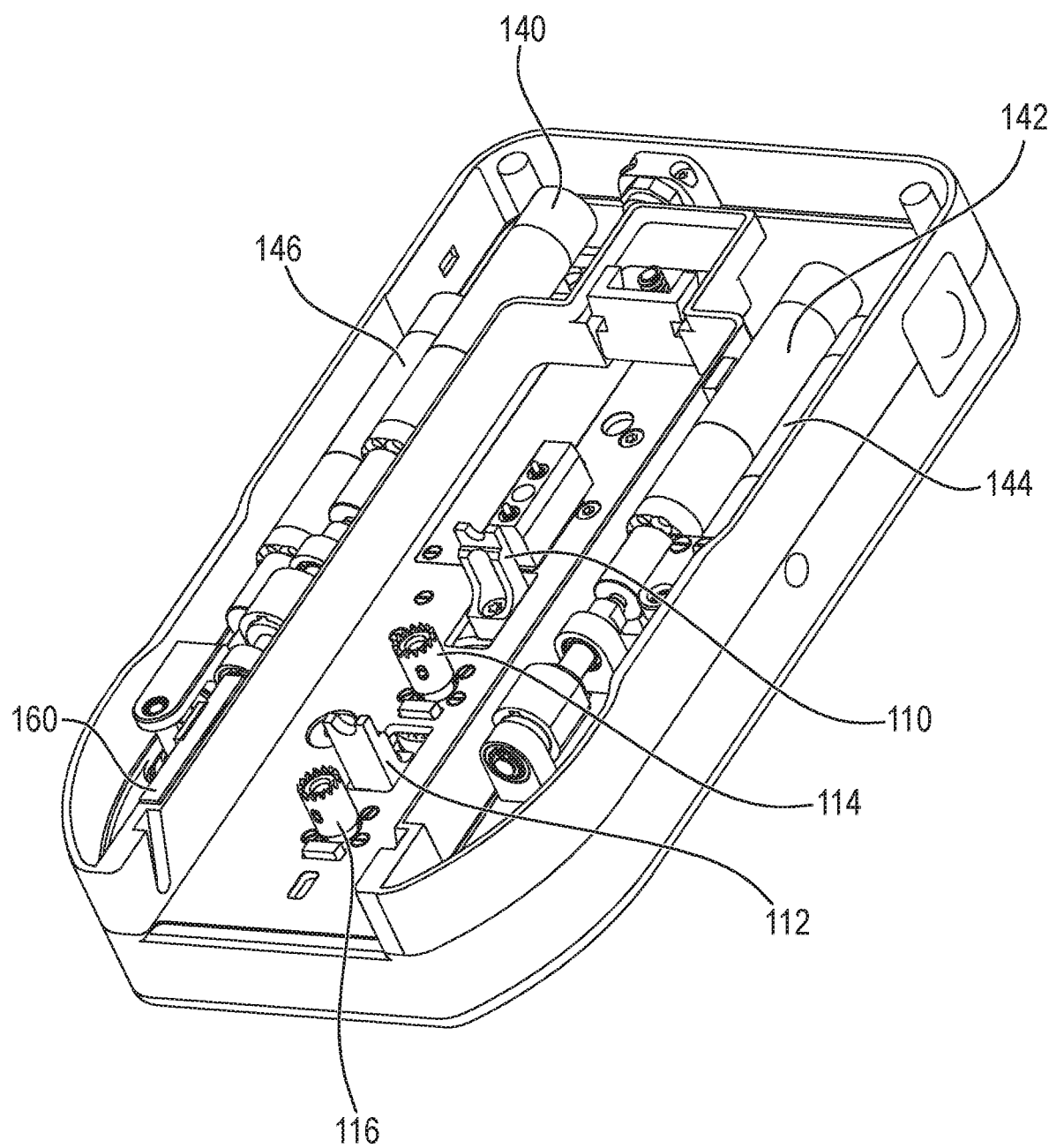
FIG. 3 shows a schematic illustration of the coupling unit of the manipulator arm with the top of the housing being removed.

FIG. 3 shows a coupling unit 100 with a removed housing top. The coupling unit 100 has altogether four drive motors 140 to 146, each of which being designed as a direct current motor with a tachometer so that the control unit 36 always knows the rotary angle of the respective drive motor 140 to 146 and may take this into account in the further control. Via a first linear linkage, the first drive motor 140 is coupled to the first translational drive element 110 which upon activation of the drive motor 140 by the control unit 36 performs a translational drive movement. Via a second linear linkage, the second drive motor 142 is coupled to the second translational drive element 112 so that upon a drive movement of the second drive motor 142 the second translational drive element 112 performs a translational drive movement. Via a first gear stage, the third drive motor 144 is coupled to the first rotational drive element 114 so that upon a drive movement of the third drive motor 144 the first rotational drive element 114 is rotated. The fourth drive motor 146 is coupled to the second rotational drive element 116 via a second gear stage so that the second rotational drive element 116 performs a rotational movement upon a drive movement of the fourth drive motor 146.

Figure 4:
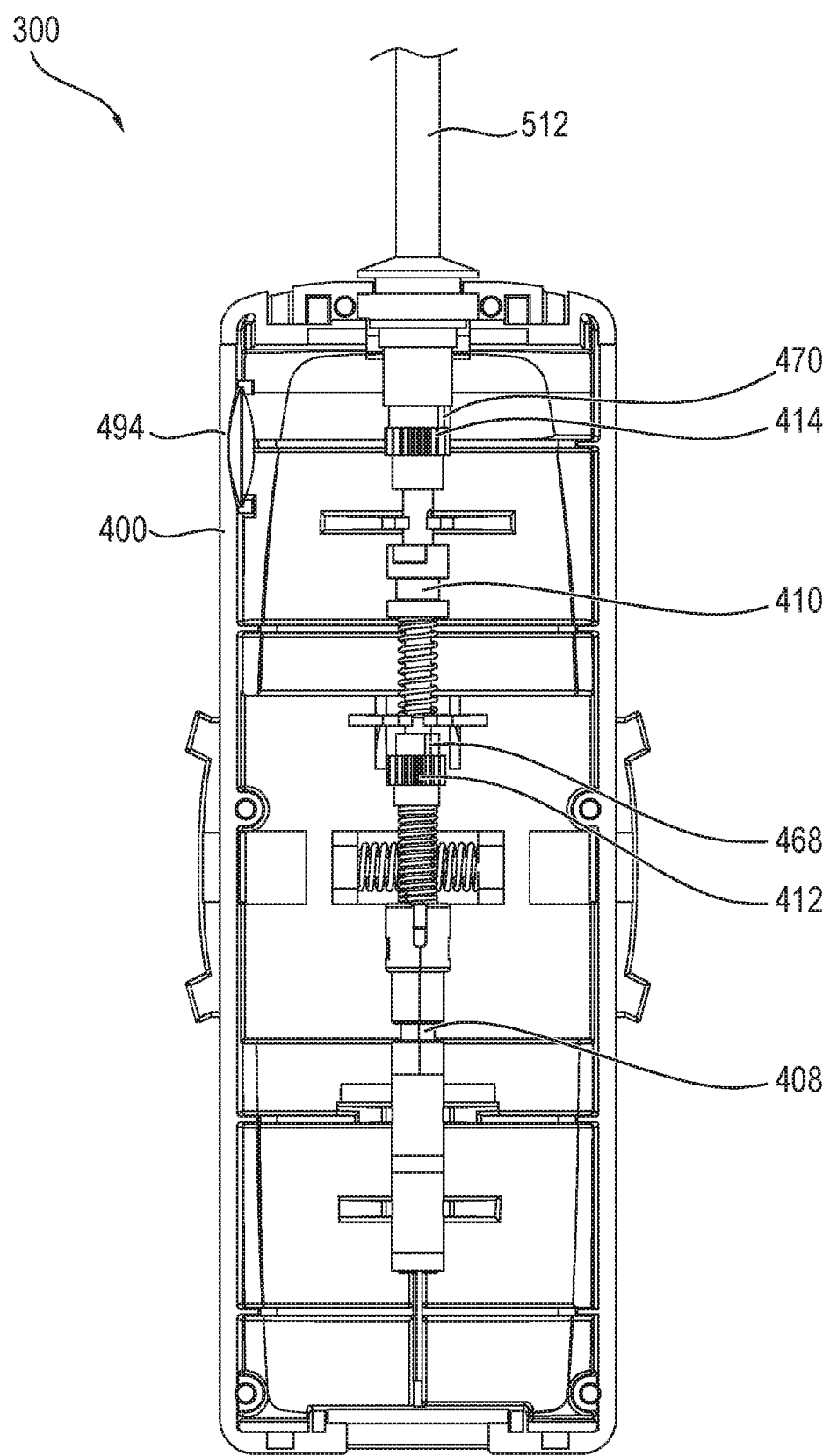
FIG. 4 shows a top view of the instrument unit with removed bottom plate.

FIG. 4 shows the instrument unit 300 in which a non-illustrated bottom plate of the sterile unit 400 has been removed. Several elements 408 to 414 are driven by way of the drive elements 110 to 116 of the coupling unit 100. The second rotationally driven element 414 formed as a gearwheel is connected to the outer instrument shaft 512 and a second angle transmitter 470 for the detection of the shaft rotation of the outer instrument shaft 512 in a rotationally fixed manner.

The second translationally driven element 410 is connected to a first inner instrument shaft so that upon a translational movement of the second translationally driven element 410 the first inner instrument shaft is moved translationally.

The first rotationally driven element 412 is connected to a first angle transmitter 468 and a second inner instrument shaft in a rotationally fixed manner. The second inner instrument shaft serves to rotate an end effector independent of the angle of rotation of the outer instrument shaft 512. The first inner instrument shaft serves to bend the end effector. Based on the robot system 10, the function of an approval control of the instrument units 300 used in an operation of a patient is described in the following.

The surgical instrument unit 300 shown in FIG. 4 is provided with a data memory 494 that is preferably configured as a radio frequency identification chip (RFID chip). During the manufacture of the surgical instrument unit 300, the data memory 494 is written with data upon a check of the surgical instrument unit 300 on a non-illustrated test bench. Provided that a functionality check has taken a positive course, a serial number, a date of manufacture, a charge number and/or a production number are generated and data with this information is stored in the data memory 494. The stored data may further comprise information on the instrument type, the maximum storage period and/or an information that the surgical instrument has not yet been used in a medical operation.

In an end check of the surgical instrument unit 300 or the surgical instrument 500, preferably taking place within a manufacturing process, a unique serial number SNo is generated for each instrument unit 300 or for each instrument 500 and is combined together with at least one further information, such as a production lot Lot or a maximum storage period SL in a first information block IB1. The first information block IB1 is provided with a checksum, encoded and stored in the surgical instrument unit 300 in a data area of the data memory 494 assigned to the information block IB1. After writing, the data area for the information block IB1 is provided with a write protection.

For use of the instrument unit 300 or the surgical instrument 500 in connection with the surgical robot system 10, a read and write device 160 reads data from the data memory 494. The read-out data are transmitted to the control unit 36 of the robot system 10 and evaluated thereby. The evaluation shall guarantee that the surgical instrument unit 300 or the surgical instrument 500 have not yet been used in another surgical operation and that the storage period lies within an admissible limit. Accordingly, a use of the surgical instrument unit 300 or the surgical instrument 500 by the control unit 36 of the robot system 10 can be approved. In the data memory 494 of the surgical instrument unit 300, the control unit 36 stores an instrument operation identification by which it is guaranteed that the instrument unit 300 can arbitrarily often be coupled, used, and decoupled to and from the robot system 10 during one and the same operation but not within another operation. Preferably, the robot system 10 generates a system operation identification which is preferably unique, is only valid for one single operation and which serves as an instrument operation identification on the instrument during the operation.

In particular, at least two information blocks D31, IB2 are stored in an encoded manner in the data memory 494. The first information block D31 comprises, for example, a checksum CHK of the first information block IB1, a serial number SNo, a production lot Lot and a maximum storage period SL.

| CHK | SNo | Lot | SL | (IB1) |
|---|---|---|---|---|

The information block IB2 may contain at least one unique operation identification (OID) or an information wildcard OIDP and/or the checksum CHK of the second information block IB2, the serial number SNo, the production lot Lot, the maximum storage period SL and/or further information. Depending on its nature, the information wildcard OIDP may itself represent a provisional compatibility criterion or contain the same.

| CHK | SNo | Lot | SL | I-OID/OIDP | (IB2) |
|---|---|---|---|---|---|

The information wildcard OIDP stored in the data memory 494 may also contain a unique operation identification OID, in particular an instrument operation identification I-OID. The unique operation identification generated by the robot system 10 and stored in the control unit 36 is also referred to as system operation identification S-OID.

Figure 5:
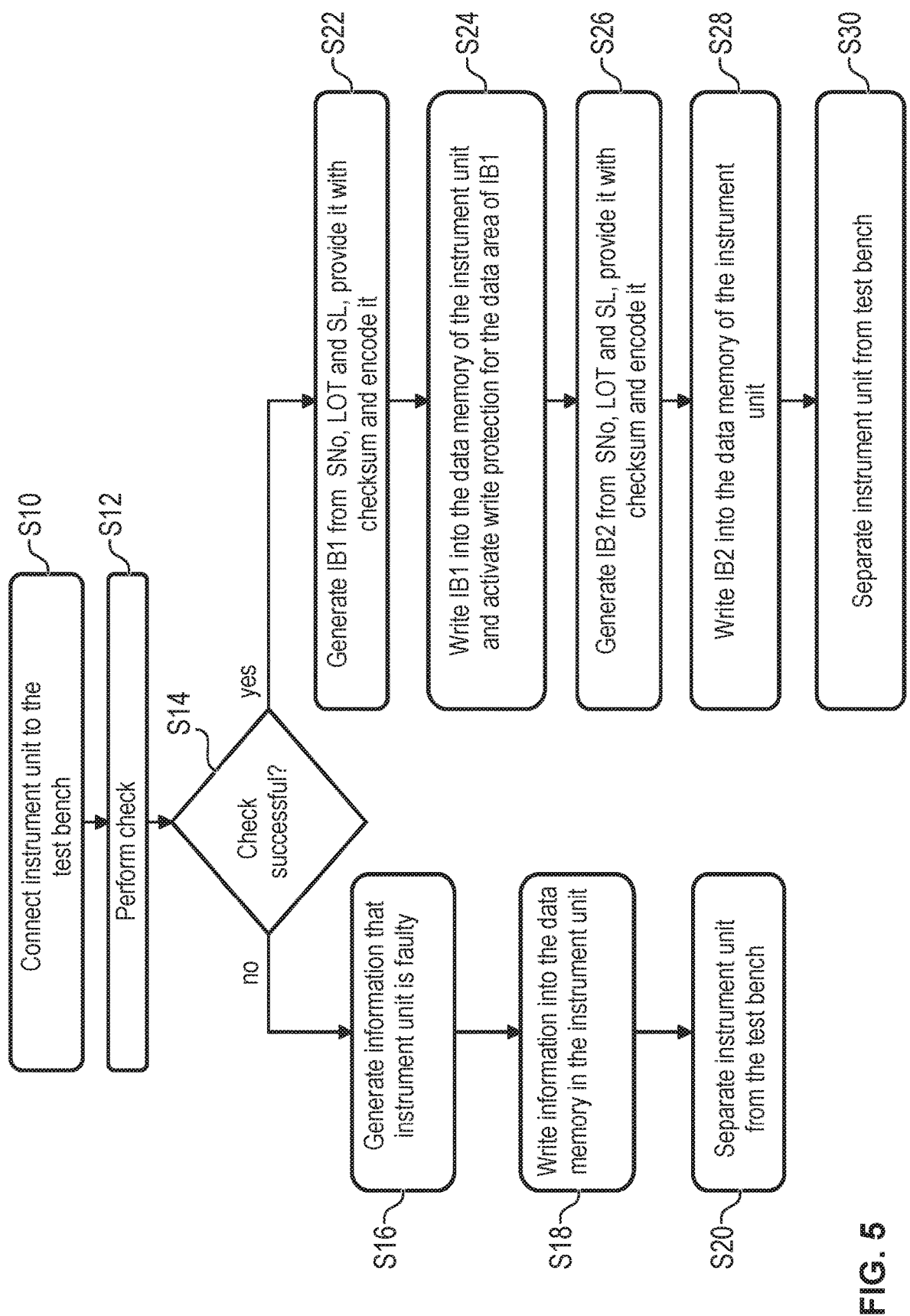
FIG. 5 shows a flow chart for illustrating the inventive method and the function of the robot system.

FIG. 5 shows a flow chart for illustrating the inventive method or the function of the robot system 10. In step S10, the surgical instrument unit 300 is connected to a non-illustrated check device which, in step S12, performs a check of the instrument unit 300 with respect to its suitability for use. In doing so, the check device checks in step S14 the surgical instrument unit 300 or the surgical instrument 500 as to whether it is fully functional, whether all constructive elements are correctly installed and whether the instrument unit 300 or the instrument 500 meets the purity and sterilization demands required for clinical use. This implies a check that the surgical instrument unit 300 or the instrument 500 to be used is an instrument unit 300 or instrument 500 not yet used in another operation.

Provided that the check according to step S14 results that the surgical instrument unit 300 or the surgical instrument 500 does not have the required suitability for use and/or does not have the required sterility, the surgical instrument unit 300 or the instrument 500 is considered faulty in step S16. A corresponding information is then stored in step S18 in the data memory 494 of the instrument unit 300. Accordingly, the surgical instrument unit 300 or the instrument 500 is discarded in step S20 after a separation from the test bench.

When the result of the check in step S14 of the surgical instrument unit 300 or the surgical instrument 500 by the check device is positive, then in step S22 data with the information block D31 are generated from the serial number SNo, the production lot Lot and the maximum storage period SL, provided with a checksum and encoded. In step S24, then the data with the information block D31 are written into the data memory 494 of the surgical instrument unit 300 and a write protection for the data area in which the data with the information block D31 are present is activated. Further, in step S26 data with the information block IB2 are generated from the information wildcard OIDP, provided with a checksum and encoded. Further, the second information block IB2 may include additional information such as the serial number SNo, the production number Lot and the maximum storage period SL. The data with the information block IB2 are then written into the data memory 494 of the surgical instrument unit 300 in step S28. Subsequently, the surgical instrument unit 300 is separated from the check device in step S30.

Figure 6:
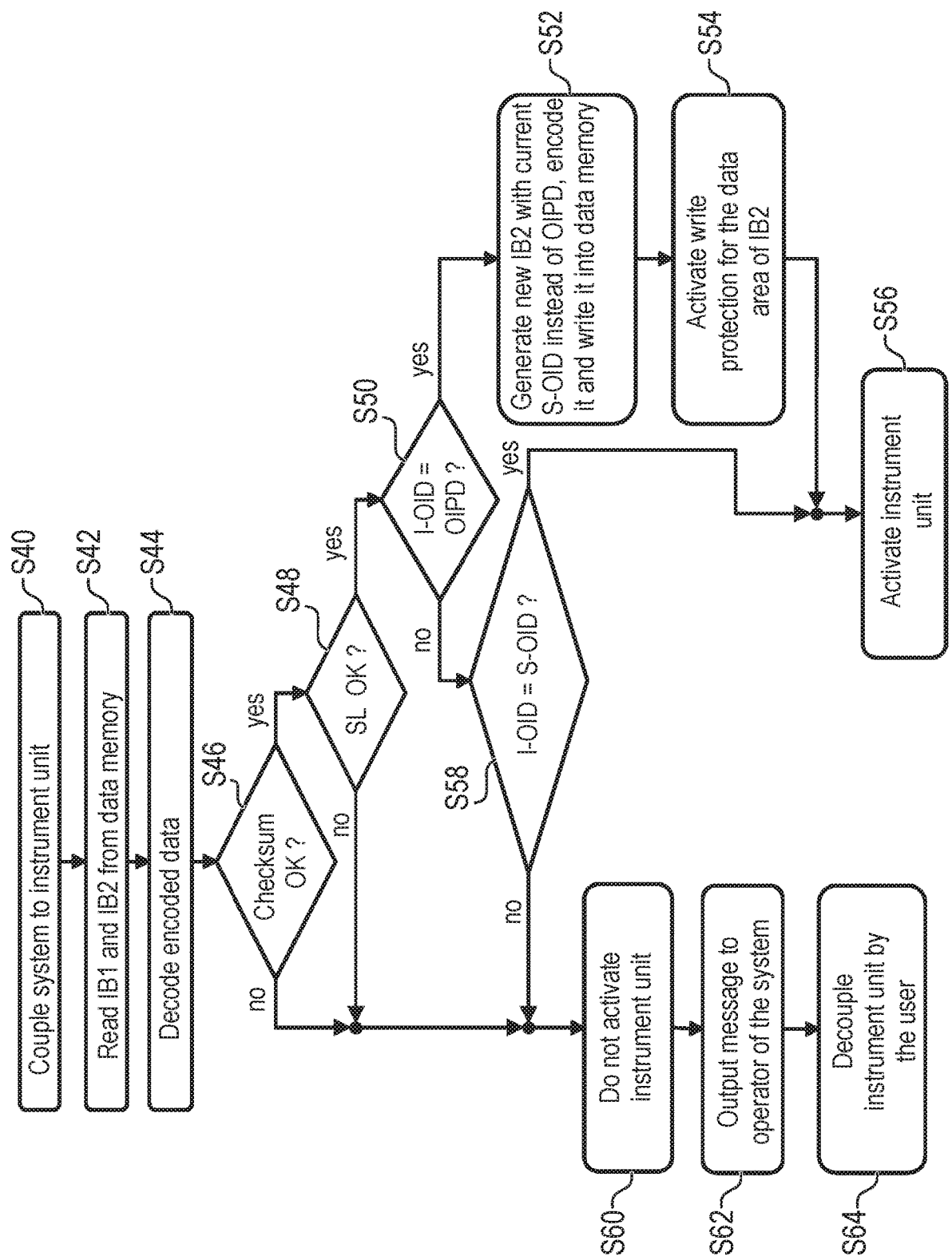
FIG. 6 shows a further flow chart for illustrating a method for the approval control of a surgical instrument to be used in the surgical robot system and for illustrating the function of the robot system.

FIG. 6 shows a further flow chart for illustrating a method for the admission control of a surgical instrument to be used in the surgical robot system 10 as well as for illustrating the function of the robot system 10.

A tested surgical instrument unit 300 described on the basis of FIG. 5 is coupled to the robot system 10 in step S40 in the sequence according to FIG. 6. First data with the information block D31 and second data with the information block IB2 are read from the data memory 494 in step S42 and the encoded first and second data are decoded in step S44. If a check in step S46 results that a checksum corresponds to an expected value, then in step S48 it is further checked whether the maximum storage period SL has not yet been exceeded. If this check in step S48 results that the maximum storage period SL has not yet expired, it is further checked in step S50 whether the instrument operation identification I-OID contained in the data is an information wildcard OIDP. If this is the case, this means that the surgical instrument unit 300 has not yet been used in an operation or a surgery. Then, in step S52 data with a new information block IB2 are generated with a current unique system operation identification S-OID generated by the robot system 10, i.e. the control unit 36, encoded and written into the data memory 494 of the surgical instrument unit 300 as second data. In the following, in step S54 a write protection for the data area of the information block IB2 is activated. Thus, in the newly generated information block IB2 the information wildcard OIDP has been replaced by the system operation identification S-OID and, after storing the newly generated information block IB2, serves as an instrument operation identification I-OID. Thereafter, the surgical instrument unit 300 is activated in step S56 for use by the robot system 10.

If, however, it is determined in the check in step S50 that the instrument operation identification I-OID contained in the data is no information wildcard OIDP, then in step S58 it is further checked whether the instrument operation identification I-OID corresponds to the system operation identification S-OID.

In case that the instrument operation identification I-OID corresponds to the system operation identification S-OID, the surgical instrument unit 300 or the instrument 500 is activated for use by the robot system 10 in step S56. This case, for example, occurs during a use of the surgical instrument unit 300 or the surgical instrument 500 in a robot system 10 during an operation, when during an operation the instrument units 300 have to be changed, i.e. a surgical instrument unit 300 or a surgical instrument 500 does not remain coupled to the robot system permanently but is separated from the robot system 10 for one or several periods of time and again coupled thereto. In such a case, the system operation identification S-OID individually generated for the current operation is already stored in the data memory 494 of the surgical instrument unit 300 in the second data block IB2 of the data memory 494 as instrument operation identification I-OID. This case may in particular occur in that all instrument units provided for a planned operation are connected to the manipulator arm 16 in preparation of the operation.

If the unique instrument operation identification I-OID stored in the data memory 494 does not correspond to the unique operation identification S-OID generated by the robot system 10, then the surgical instrument unit 300 is not activated in step S60 for use by the robot system 10. Further, in step S62 a message is output to an operator or user of the robot system 10. The surgical instrument unit 300 is then decoupled from the coupling unit 100 of the robot system 10 by the operator or user in step S64. Further, a driving of the manipulator arm 16 to which this instrument unit 300 is connected is prevented by the control unit 36.

The steps S60 to S64 are also run through when the check according to step S46 determines an incorrect checksum or when it is determined in the check in step S48 that the maximum storage period SL has already expired.

In the case of a first time use of the surgical instrument unit 300 in a surgical robot system 10, first data with the first information block IB1 and second data with the second information block IB2 are read from the data memory 494 and decoded after coupling of the surgical instrument unit 300. Further, on the basis of a checksum the validity of the data is checked. In the case of a positive check the content is checked as to whether redundant device information of the two information blocks IB1 and IB2 are identical. Further, it is checked whether the maximum storage period SL has not yet expired and whether the surgical instrument unit 300 or the instrument 500 has not yet been used in an operation.

If it results from this check that the instrument unit 300 has not yet been used in an operation, then no system operation identification S-OID generated by a robot system 10 can have been stored in the corresponding area of the information block IB2 as instrument identification I-OID yet. The second data with the information block IB2 are then newly generated by using a current valid unique operation identification S-OID generated by the robot system 10, provided with a checksum, encoded and stored in the data memory 494. Further, a write protection for the data area of the data of the information block IB2 in the data memory 494 is activated. As a result, it is achieved that the data area with the second data of the information block IB2 is only readable. Subsequently, the coupled instrument unit 300 is activated for a current upcoming operation.

In the case of a repeated use of a so-configured surgical instrument unit 300 in a surgical robot system 10, the first data with the information block IB1 and the second data with the information block IB2 are read from the data memory and decoded after coupling of the surgical instrument unit 300. On the basis of a checksum it is checked whether the data are valid. When the check is positive a check is made as to whether the corresponding data of the two information blocks IB1 and IB2 are identical.

Further, it is checked whether a maximum storage period SL has not yet expired and whether the instrument unit 300 or the instrument 500 has not yet been used. In the case that the surgical instrument unit 300 or the instrument 500 have already been used, the unique instrument operation identification I-OID stored in the instrument unit 300 is compared with the unique system operation identification S-OID generated by the robot system 10.

If the system operation identification S-OID and the instrument operation identification I-OID correspond, the surgical instrument unit 300 is approved for use by the control unit 36. If the unique system operation identification S-OID generated on the robot system 10 does not correspond to the unique instrument operation identification I-01D, the surgical instrument unit 300 is not approved for use and the user is informed about this. In this way, it is prevented that a surgical instrument unit 300 or a surgical instrument 500 which has already been used in an operation marked by the instrument operation identification I-OID is again used for another operation.

The data memory 494 can be a data memory of an RFID chip which is writable and readable with the aid of a RFID read and write unit. In other embodiments, the instrument unit 300 may comprise other memories which serve as data memories 494, in particular a memory readable and/or writable via wireless LAN or Bluetooth.

The invention claimed is:

1. A method for the approval control of a surgical instrument to be used in a surgical robot system, the surgical instrument having a data memory in which first data with first information on the surgical instrument and second data with information on at least one compatibility criterion of the surgical robot system with respect to the surgical instrument are stored, the method comprising:
coupling the surgical instrument to the surgical robot system;
reading out the first data from the data memory;
checking whether the surgical instrument is suitable for use in the surgical robot system based on the first information contained in the first data,
if, upon checking, the surgical instrument is determined to be suitable for use in the surgical robot system, reading out the second data from the data memory; and
checking whether at least the one compatibility criterion meets at least one compatibility condition stored in the surgical robot system in a preset manner based on the second information contained in the second data;
wherein the second data comprise an information wildcard for adding a system operation identification that it is checked as a compatibility condition whether the information wildcard is present in the second data, that a system operation identification for a unique identification of a single operation in which the surgical instrument shall be used is predetermined by the robot system as a compatibility criterion, and that the predetermined system operation identification is stored in the area of the information wildcard of the second data as an instrument operation identification;
wherein the surgical instrument is approved for use by the surgical robot system only when the compatibility criterion meets the at least one compatibility condition stored in the preset manner.

2. The method according to claim 1, characterized in that the information wildcard itself represents and/or contains a provisional compatibility criterion and that the presence of the provisional compatibility criterion is checked as a compatibility condition.

3. The method according to claim 1, characterized in that as a compatibility condition the correspondence of the system operation identification predetermined by the surgical robot system and the instrument operation identification contained in the second data as a compatibility criterion is checked.

4. The method according to claim 1, characterized in that the first data contain at least one of a serial number identifying the surgical instrument at least with respect to its function, a date of manufacture and/or a maximum storage period of the surgical instrument or an expiry date of the surgical instrument and that as a compatibility condition it is checked whether one of the maximum storage period or the expiry data has been exceeded.

5. The method according to claim 1, characterized in that at least one of the first or the second data contains a checksum for its verification.

6. The method according to claim 1, characterized in that the at least one of first data or the second data is provided with a write protection, wherein the write protection of the second data is preferably activated after storage of the system operation identification, wherein the write protection is no longer deactivatable after activation.

7. The method according to claim 1, characterized in that the first data contain information with a provisional compatibility criterion.

8. A surgical robot system having at least one manipulator for moving and/or actuating a surgical instrument, which is in particular intended for use in one single operation, a control unit for controlling the manipulator, and a read and write device for reading and storing data of a data memory of the surgical instrument, wherein the read and write device is configured to read first data with first information on the surgical instrument from the data memory and to transmit them to the control unit in connection with a coupling of the surgical instrument with the robot system, wherein:
the data memory of the surgical instrument contains second data with information on at least one compatibility criterion of the surgical robot system with respect to the surgical instrument,
the read and write device is configured to read at least the first data from the data memory and to transmit them to the control unit in connection with the coupling of the surgical instrument with the robot system,
the control unit is configured to check with the aid of the first information contained in the first data whether the surgical instrument is suitable for use in the surgical robot system,
the read and write device reads the second data from the data memory and transmits them to the control unit when, upon checking, the control unit has determined a suitability of the surgical instrument for use in the surgical robot system,
the second data contain an information wildcard for adding a system operation identification that the control unit checks as a compatibility condition the presence of the information wildcard in the second data, that the control unit predetermines a system operation identification for the unique identification of a single operation in which the surgical instrument is to be used, and that the read and write device stores the predetermined system operation identification in the area of the information wildcard of the second data as an instrument operation identification,
the control unit is configured to check on the basis of the second information contained in the second data whether at least the one compatibility criterion meets at least one compatibility condition stored in the control unit in a preset manner, and the control unit approves the surgical instrument for use by the surgical robot system only when the compatibility criterion meets the at least one compatibility condition stored in a preset manner.

9. The surgical robot system according to claim 8, characterized in that the information wildcard represents and/or contains a provisional compatibility criterion and that as a compatibility condition the presence of the provisional compatibility criterion is checked.

10. The surgical robot system according to claim 8, characterized in that the control unit checks as a compatibility condition the correspondence of the system operation identification predetermined by the surgical robot system with the instrument operation identification contained in the second data as a compatibility criterion.

11. The surgical robot system according to claim 8, characterized in that a check device for checking the surgical instrument stores at least one of the first or second data in the data memory of the surgical instrument unit prior to an operation.

12. The surgical robot system according to claim 8, characterized in that the read and write device is configured to read the first data from the data memory when coupling the surgical instrument with the robot system.

13. The surgical robot system according to claim 8, characterized in that the first data contain at least one of a serial number identifying the surgical instrument at least with respect to its function, a date of manufacture and/or a maximum storage period of the surgical instrument or an expiry date of the surgical instrument and that as a compatibility condition it is checked whether one of the maximum storage period or the expiry data has been exceeded.

14. The surgical robot system according to claim 8, characterized in that at least one of the first or the second data contains a checksum for its verification.

15. The surgical robot system according to claim 8, characterized in that the at least one of first data or the second data is provided with a write protection, wherein the write protection of the second data is preferably activated after storage of the system operation identification, wherein the write protection is no longer deactivatable after activation.

16. The surgical robot system according to claim 8, characterized in that the first data contain information with a provisional compatibility criterion.

* * * * *